US012714800B2

(12) United States Patent
Chin et al.

(10) Patent No.: US 12,714,800 B2
(45) Date of Patent: Aug. 25, 2026

(54) SYSTEM FOR OPERATING SYRINGE

(71) Applicants: Se Hoon Chin, Seongnam-si (KR); Kyung Suk Jin, Incheon (KR)

(72) Inventors: Se Hoon Chin, Seongnam-si (KR); Kyung Suk Jin, Incheon (KR)

( * ) Notice: Subject to any disclaimer, the term of this patent is extended or adjusted under 35 U.S.C. 154(b) by 760 days.

(21) Appl. No.: 18/044,857

(22) PCT Filed: Mar. 24, 2021

(86) PCT No.: PCT/KR2021/003640
§ 371 (c)(1),
(2) Date: Mar. 10, 2023

(87) PCT Pub. No.: WO2022/055061
PCT Pub. Date: Mar. 17, 2022

(65) Prior Publication Data

US 2023/0364350 A1 Nov. 16, 2023

(30) Foreign Application Priority Data

Sep. 11, 2020 (KR) ........................ 10-2020-0116782

(51) Int. Cl.
*A61M 5/315* (2006.01)

(52) U.S. Cl.
CPC ..... *A61M 5/31573* (2013.01); *A61M 2205/19* (2013.01)

(58) Field of Classification Search
CPC .......... A61M 5/31573; A61M 2205/19; A61M 5/1407; A61M 5/1456; A61M 5/172;
(Continued)

(56) References Cited

U.S. PATENT DOCUMENTS 6,269,340 B1 * 7/2001 Ford ...................... G16H 40/40 604/890.1
6,520,928 B1 2/2003 Junior
(Continued)

FOREIGN PATENT DOCUMENTS

CN 102105187 A 6/2011
CN 109742578 A 5/2019
(Continued)

OTHER PUBLICATIONS

Office Acton received in Japanese Application No. 2023-515871 dated Mar. 12, 2024 in 8 pages.
(Continued)

*Primary Examiner* — James D Ponton
(74) *Attorney, Agent, or Firm* — Knobbe, Martens, Olson & Bear, LLP

(57) ABSTRACT

Proposed is a system for operating a syringe. The system includes an apparatus for operating a syringe in which a syringe filled with one or more fluids is mounted and that includes a motor configured to selectively discharge the one or more fluids filled in the syringe by moving forward and backward a piston of the syringe, and a controller configured to control movement of the piston of the syringe through the motor, in which the controller moves the piston to follow a predetermined motion on the basis of a set mode when recognizing a request to operate or stop the apparatus for operating a syringe.

15 Claims, 5 Drawing Sheets

(58) Field of Classification Search

CPC .......... A61M 5/204; A61M 2005/1787; A61M 2205/078; A61M 2205/586; A61M 5/2066; A61M 5/3129; A61M 5/20; A61M 5/19; A61M 5/2448; A61M 5/3137; A61M 5/31576; A61M 5/3158; A61M 2005/2437; A61B 90/50

See application file for complete search history.

(56) References Cited

U.S. PATENT DOCUMENTS

| | | | |
|---|---|---|---|
| 10,646,660 B1 | 5/2020 | Hochman et al. | |
| 2003/0028144 A1 | 2/2003 | Duchon et al. | |
| 2016/0030663 A1 | 2/2016 | Adaniya et al. | |
| 2016/0228645 A1* | 8/2016 | Patrick | A61M 19/00 |

FOREIGN PATENT DOCUMENTS

| | | | |
|---|---|---|---|
| EP | 0538174 | A1 | 4/1993 |
| JP | 2004-236734 | A | 8/2004 |
| JP | 2005-027805 | A | 2/2005 |
| JP | 2005-152505 | A | 6/2005 |
| JP | 2007-522877 | A | 8/2007 |
| JP | 2019-166393 | A | 10/2019 |
| JP | 2023-543405 | A | 10/2023 |
| KR | 10-2011-0037979 | A | 4/2011 |
| KR | 10-1440838 | B1 | 9/2014 |
| KR | 10-1648056 | B1 | 8/2016 |
| KR | 10-1887641 | B1 | 8/2018 |
| WO | 94/04415 | A1 | 8/1993 |
| WO | WO 2007/133942 | A2 | 11/2007 |
| WO | WO 2019/181239 | A1 | 9/2019 |

OTHER PUBLICATIONS

Extended European Search Report in European Application No. 21866933.1 dated Jul. 23, 2024.

Office Action received in Chinese Application No. 202180062586.2 dated Jul. 18, 2024.

Office Action received in Japanese patent application No. 2024-095458 dated Mar. 18, 2025.

* cited by examiner

FIG. 9

SYSTEM FOR OPERATING SYRINGE

FIELD

The present invention relates a system for operating a syringe and, more particularly, to a system for operating a syringe, the system being able to reduce errors in surgical procedure and enable a more convenient surgical procedure when performing dermal regeneration.

BACKGROUND ART

Skin is composed of dermis and epidermis, in which the dermis is the skin under the epidermal layer and is composed of collagen, elastin, and matrix protein that determine elasticity of the skin. As aging progresses, cell regeneration of the dermal layer slows and production of hyaluronic acid slows, so fibers related to elasticity of the skin break or lose elasticity. Accordingly, regeneration of damaged dermis may be considered as the core of skin care.

Recessed scars and deep wrinkles that are difficult to treat can be treated by tearing first the dermal layer through injection of a small amount of gas into the dermal layer and then injecting a small amount liquid into the torn dermal layer such that physical stimulation, chemical stimulation, and biological stimulation simultaneously occur and a great number of collagen fiber tissues are produced at a desired part.

Accordingly, in order to achieve such self-dermal regeneration, it is required to alternately inject gas and liquid with one syringe inserted, and to this end, there was a need for a syringe having a specific structure and a syringe for dermal regeneration has been developed.

However, in a surgical procedure using a syringe for dermal regeneration, when the operation of the syringe is controlled by a hand of a person to treat wide and many wrinkles or recessed scars, there is a problem that large differences are generated in the result of surgical procedure, depending on the ability of operators. Further, even though an operator is skillful, there is a problem that it takes long time to treat wide and many wrinkles or recessed scars and the surgical procedure process is not convenient.

Further, since it is required to infinitely reciprocate the piston of a syringe forward and backward, a pain is caused at the joints of the thumb and the index finger that have to strongly hold a ring of the piston. Further, in order to achieve the fundamental objective of a syringe for dermal regeneration, an operator has to tear first the dermal layer by injecting a desired small amount of gas into a desired part and then accurately inject a desired amount of liquid into the torn dermal layer such that physical stimulation, chemical stimulation, and biological stimulation simultaneously occur and a great number of collagen fiber tissues are produced at the desired part. Accordingly, there is a problem that the method of operating a syringe for dermal regeneration should be changed in accordance with the states of scars or wrinkles.

Accordingly, in order to equalize severe differences in surgical procedure result due to ability differences of operators in manual surgical procedures, remove the physical pain at the hand of an operator that is used to perform a surgical procedure on a wide part, and minimize the time for which a patient feels pain by reducing a surgical procedure time, it was required to automate the forward and backward movement of the piston of a syringe for dermal regeneration.

Further, it was required to specify a method of automatically operating a syringe for dermal regeneration that can maximize the effect of self-dermal regeneration by minimizing the differences in proficiency of a surgical procedure without an individual difference in accordance with the depths, areas, etc. of scars or wrinkles by specifying and programming in advance whether to move a piston backward and then forward or move a piston forward and then backward, as necessary, or not only the order of moving a piston forward and backward, but relative backward movement distance and forward movement distance.

The description provided above as a related art of the present invention is just for helping understand the background of the present invention and should not be construed as being included in the related art known by those skilled in the art.

DISCLOSURE

Technical Tasks

An objective of the present invention proposed to solve the problems described above is to provide a system for operating a syringe, the apparatus being able to reduce errors in surgical procedure and enable a convenient and quick surgical procedure when performing dermal regeneration.

Technical Solution

In order to achieve the objectives, a system for operating a syringe according to the present invention includes: an apparatus for operating a syringe in which a syringe filled with one or more fluids is mounted and that includes a motor configured to selectively discharge the one or more fluids filled in the syringe by moving forward and backward a piston of the syringe; and a controller configured to control movement of the piston of the syringe through the motor, in which the controller moves the piston to follow a predetermined motion on the basis of a set mode when recognizing a request to operate or stop the apparatus for operating a syringe.

The system may further include a pedal switch configured to transmit requests to operate and stop the apparatus for operating a syringe to the controller.

The system may further include a setter configured to set motions of the piston, in which a first mode or a second mode can be set through the setter.

When the pedal switch is pressed down and released with the first mode set, the controller may move the piston backward by a preset first distance, forward by the sum of the preset first distance and a preset second distance, backward by a preset third distance, and then forward by a distance shorter than or the same as the third distance.

The syringe may be filled with a first fluid and a second fluid, and the first distance may be set on the basis of the amount of the second fluid that is discharged from the syringe and the second distance may be set on the basis of the amount of the first fluid that is discharged from the syringe.

When the second mode is set, the controller may move the piston backward by a preset first distance and then forward by the sum of the preset first distance and a second preset distance when the pedal switch has been pressed, and the controller may move the piston backward by a preset third distance and then forward by a distance shorter than or the same as the third distance when the pedal switch is released.

When the pedal switch has been pressed down with the second mode set, the controller may repeat an operation of moving the piston backward by the preset first distance and then forward by the sum of the preset first distance and the preset second distance until the pedal switch is released.

The system may further include a main body including a second fluid storage configured to store the second fluid to be supplied to the syringe.

The system may further include a linkage extending upward from the main body and then extending downward, and configured to maintain the apparatus for operating a syringe hung in the air with a needle facing down.

The linkage may connect the apparatus for operating a syringe and the main body to each other, maintain the apparatus for operating a syringe hung in the air, and adjust a position and an angle with the apparatus for operating a syringe hung in the air.

The linkage may include:

a first link extending upward from an upper end of the main body; a second link extending downward from an upper end of the first link; and a third link extending downward from a lower end of the second link and configured to fix the apparatus for operating the syringe at an end thereof.

The apparatus for operating syringe may include one or more of:

a body in which a syringe filled with one or more fluids is mounted; an actuator disposed behind the body and configured to selectively discharge the one or more fluid filled in the syringe by moving forward and backward a piston; a holder provided on a bottom of the body, configured to hold a finger or a back of a hand of a user, and formed in a curved shape having a predetermined area to be able to be supported on the finger or the back of the hand of the user; a second fluid supplier disposed at a bottom of the actuator, connected to a second fluid storage, connected to a second fluid injection port, and configured to supply a second fluid to an outer barrel through the second fluid injection port; and a cover having a shape surrounding a top of the syringe, hinged at a side to the body, and configured to cover the syringe mounted in the body by rotating through a hinge, thereby fixing the syringe with the body.

The syringe may include:

a syringe body composed of an inner barrel that is filled with a first fluid and an outer barrel that is filled with a second fluid and surrounds the inner barrel at a predetermined distance from the inner barrel, and having a filling space configured to be filled with a second fluid between the inner barrel and the outer barrel;

and a second fluid injection port formed at the syringe body and communicating with the filling space such that the filling space is filled with the second fluid.

A mounting protrusion for mounting in the body may be formed on a bottom of the syringe and one or more mounting grooves may be formed in the body at a position corresponding to a position of the mounting protrusion when the syringe is mounted.

The holder may include:

one or more of a first holder disposed at a front portion of the bottom of the body, having a predetermined area to be held on a portion of the finger, and having a curvature in the predetermined area to surround the portion of the finger, and a second holder disposed at a rear portion of the bottom of the body, having a predetermined area to be held at a portion between a thumb and an index finger of the back of the hand, and having a curvature in the predetermined area to surround the portion between the thumb and the index finger.

The main body may further include a first hinge portion hinged to the cover at a side and a first fixing portion configured to fix the cover at another side, the cover may include a second hinge portion coupled to the first hinge portion at a side and a second fixing portion fixed to the first fixing portion at another side, and the first hinge portion and the second hinge portion may share a hinge shaft and may rotate on the hinge shaft, and the first fixing portion and the second fixing portion may be coupled to each other, thereby fixing the syringe.

The first hinge portion and the second hinge portion may protrude to a side, the first fixing portion and the second fixing portion may protrude to another side, and a thumb and an index finger may be supported on the first hinge portion and the second hinge portion, and the first fixing portion and the second fixing portion.

A tube groove configured to prevent folding of a tube connecting a second fluid injection port and a second fluid supplier to each other, and to fix the tube may be formed on an inner surface of the cover.

Advantageous Effects

According to the system for operating a syringe of the present invention, it is possible to reduce errors in surgical procedure and enable a more convenient surgical procedure when performing dermal regeneration.

That is, it is possible to equalize severe differences in surgical procedure result due to ability differences of operators in manual surgical procedures, remove the physical pain at the hand of an operator that is used to perform a surgical procedure on a wide part, and minimize the time for which a patient feels pain by reducing a surgical procedure time.

Further, it is possible to maximize the effect of self-dermal regeneration by minimizing the differences in proficiency of a surgical procedure without an individual difference in accordance with the depths, areas, etc. of scars or wrinkles by specifying and programming in advance whether to move a piston backward and then forward or move a piston forward and then backward, as necessary, or not only the order of moving a piston forward and backward, but relative backward movement distance and forward movement distance.

DESCRIPTION OF DRAWINGS

FIG. 9 is a view illustrating the configuration of a syringe of the system for operating a syringe according to an embodiment of the present invention.

BEST MODE

A system for operating a syringe according to the present invention includes: an apparatus for operating a syringe in which a syringe filled with one or more fluids is mounted and that includes a motor configured to selectively discharge the one or more fluids filled in the syringe by moving forward and backward a piston of the syringe; and a controller configured to control movement of the piston of the syringe through the motor, in which the controller can move the piston to follow a predetermined motion on the basis of a set mode when recognizing a request to operate or stop the apparatus for operating a syringe

MODE FOR INVENTION

Hereafter, apparatuses for operating a syringe according to exemplary embodiments of the present invention are described with reference to drawings.

Figure 1:
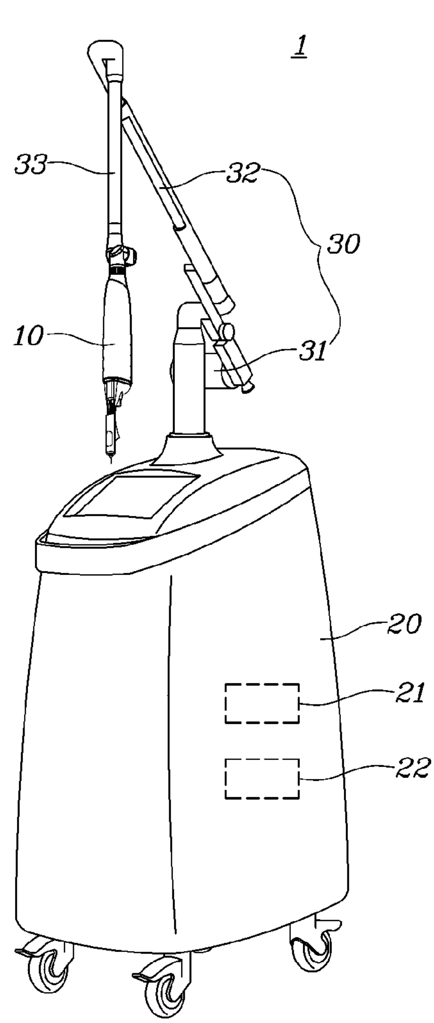
FIG. 1 is a view showing a system for operating a syringe according to an embodiment of the present invention.
Figure 2:
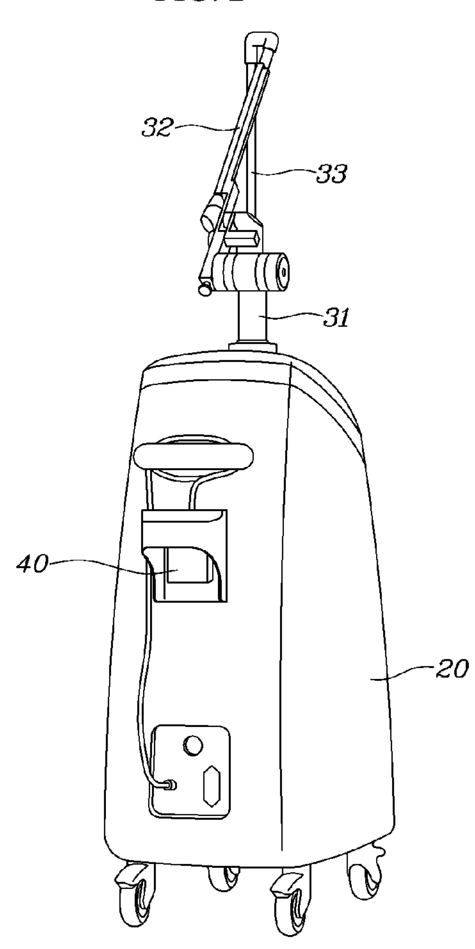
FIG. 2 is a view showing the rear surface of the system for operating a syringe according to an embodiment of the present invention.
Figure 3:
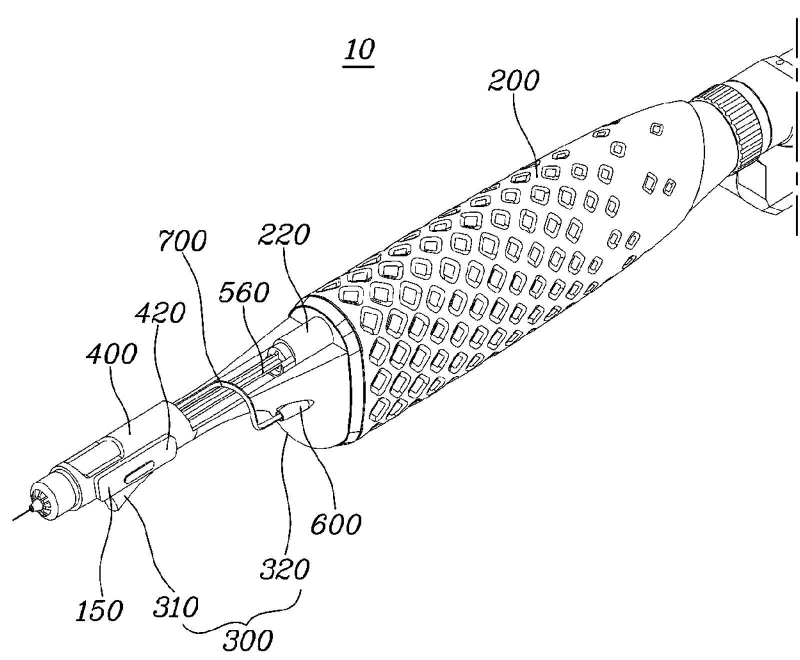
FIG. 3 is a view showing an apparatus for operating a syringe of the system for operating a syringe according to an embodiment of the present invention.
Figure 4:
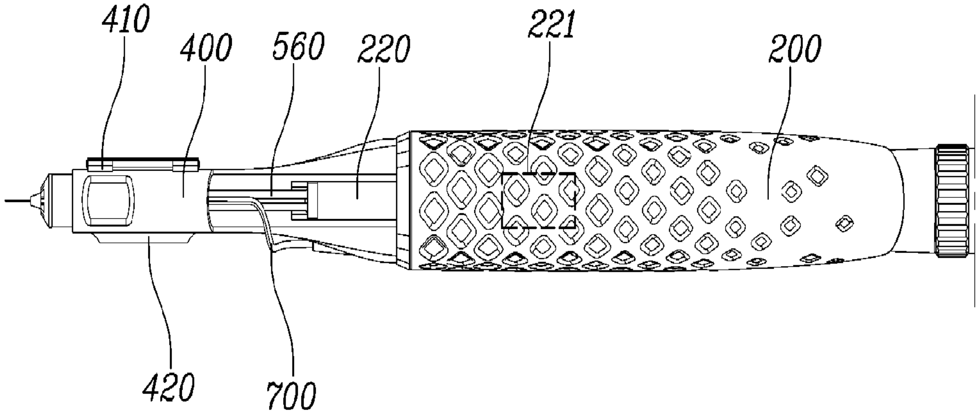
FIG. 4 is a view showing from above the apparatus for operating a syringe of the system for operating a syringe according to an embodiment of the present invention.
Figure 5:
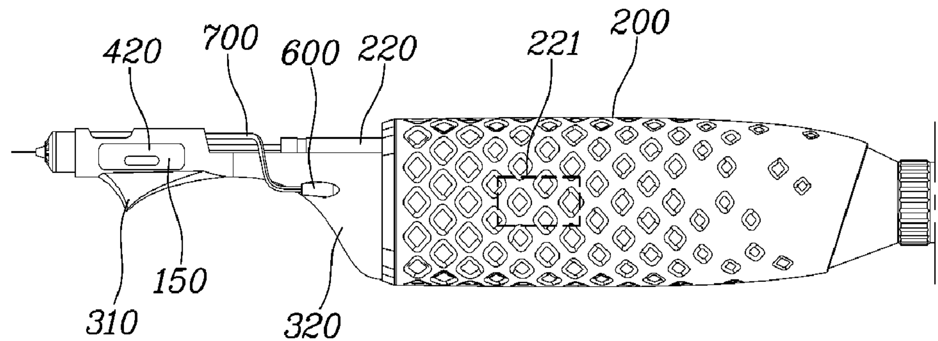
FIG. 5 is a view showing from a side the apparatus for operating a syringe of the system for operating a syringe according to an embodiment of the present invention.
Figure 6:
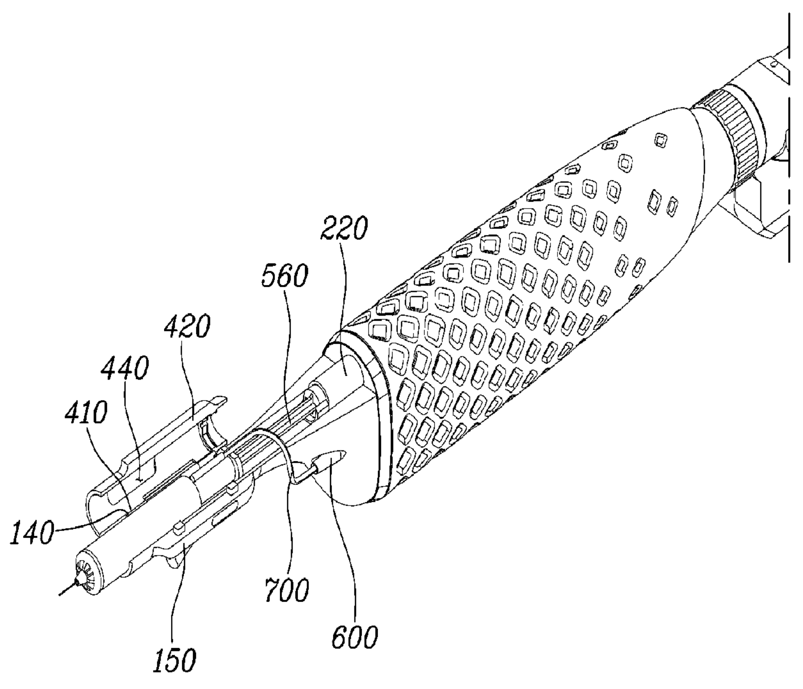
FIG. 6 is a view showing the state in which a cover is open in the apparatus for operating a syringe of the system for operating a syringe according to an embodiment of the present invention.
Figure 7:
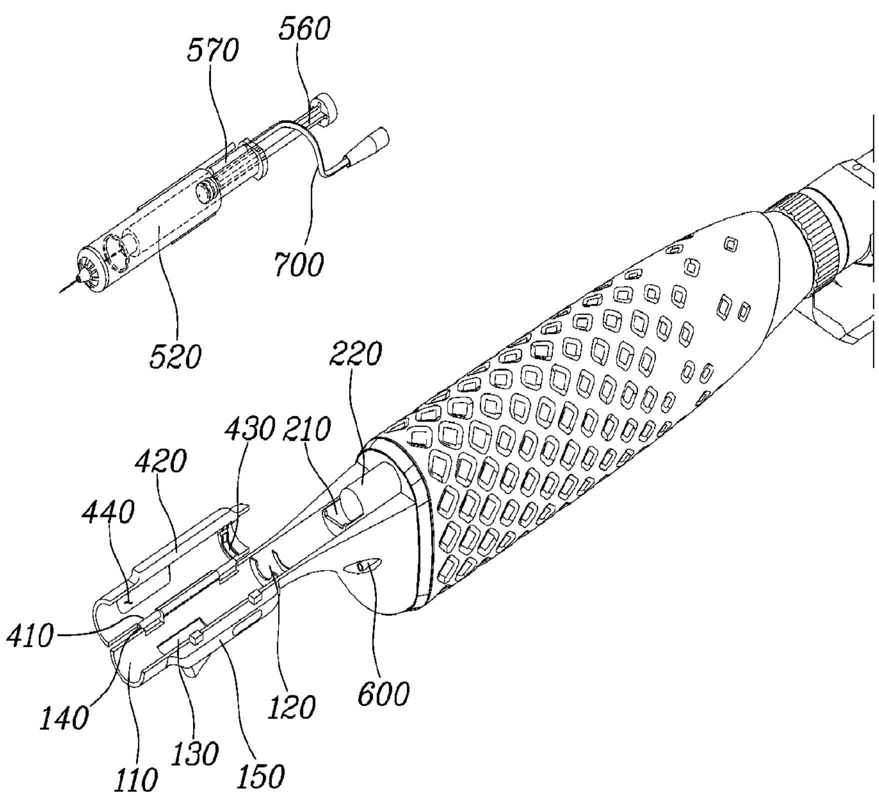
FIG. 7 is a view showing the state in which a syringe has been decoupled in the apparatus for operating a syringe of the system for operating a syringe according to an embodiment of the present invention.
Figure 8:
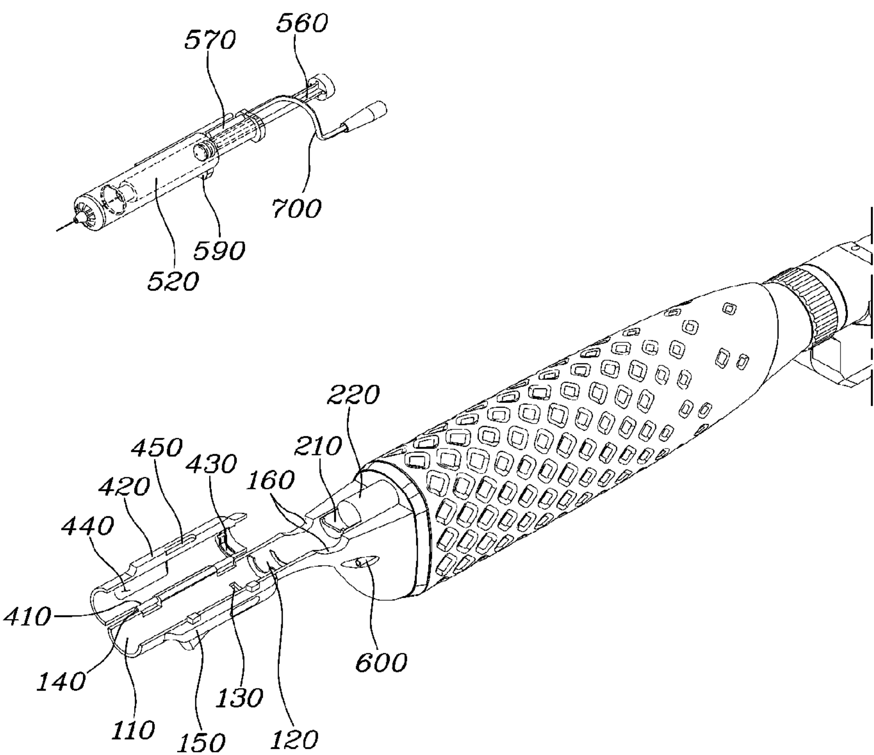
FIG. 8 is a view showing the state in which a syringe has been decoupled in an apparatus for operating a syringe of the system for operating a syringe according to another embodiment of the present invention.
Figure 9:
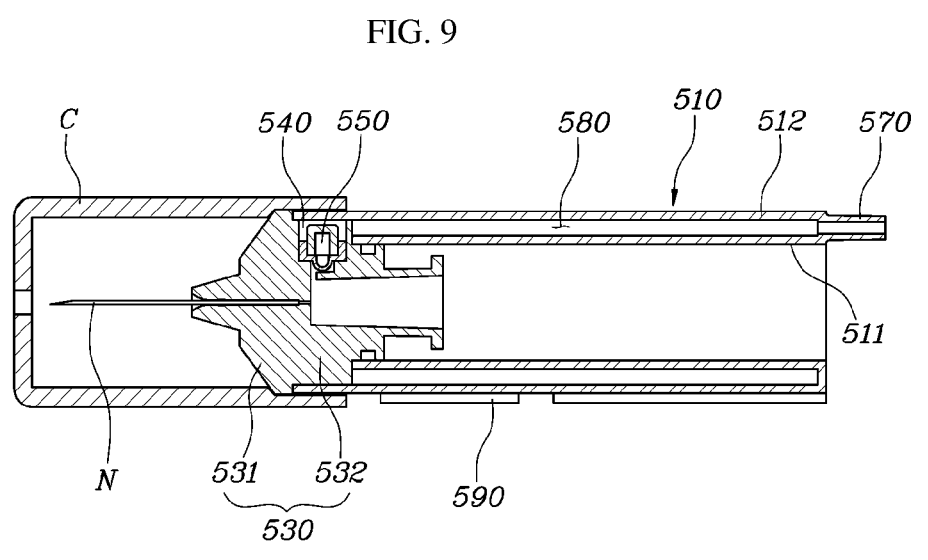

FIG. 1 is a view showing a system for operating a syringe according to an embodiment of the present invention and FIG. 2 is a view showing the rear surface of the system for operating a syringe according to an embodiment of the present invention. FIG. 3 is a view showing an apparatus for operating a syringe of the system for operating a syringe according to an embodiment of the present invention, FIG. 4 is a view showing from above the apparatus for operating a syringe of the system for operating a syringe according to an embodiment of the present invention, FIG. 5 is a view showing from a side the apparatus for operating a syringe of the system for operating a syringe according to an embodiment of the present invention, FIG. 6 is a view showing the state in which a cover is open in the apparatus for operating a syringe of the system for operating a syringe according to an embodiment of the present invention, FIG. 7 is a view showing the state in which a syringe has been decoupled in the apparatus for operating a syringe of the system for operating a syringe according to an embodiment of the present invention, FIG. 8 is a view showing the state in which a syringe has been decoupled in an apparatus for operating a syringe of the system for operating a syringe according to another embodiment of the present invention, and FIG. 9 is a view illustrating the configuration of a syringe of the system for operating a syringe according to an embodiment of the present invention.

Referring to FIGS. 1 and 2, a system 1 for operating a syringe according to an embodiment of the present invention may include: an apparatus 10 for operating a syringe in which a syringe 500 filled with one or more fluids is mounted and that includes a motor selectively discharging the one or more fluids filled in the syringe 500 by moving forward and backward a piston 560 of the syringe 500; and a controller 22 controlling movement of the piston 560 of the syringe 500 through the motor 221. In this configuration, a controller 22 can move the piston 560 to follow a predetermined motion on the basis of a set mode when recognizing a request to operate or stop the apparatus 10 for operating a syringe.

Further, the system for operating a syringe may further include a body 20 having a second fluid storage that stores a second fluid to be supplied to the syringe 500, a linkage 30 extending upward from the body 20 and then extending down such that the apparatus 10 for operating a syringe is hung in the air with a needle facing down, and a pedal switch 40.

Referring to FIGS. 3 to 8, the apparatus 10 for operating a syringe may include one or more of a body 100, an actuator 200, a holder 300, a cover 400, and a second fluid supplier 600.

A syringe 500 filled with one or more fluids may be mounted on the body 100. In detail, referring to FIG. 7, the body 100 may include a first seat 110 that has a shape surrounding the syringe 500 and in which the syringe 500 is seated, and a second seat 120 that is stepped from the first seat 110 and in which a cylinder 520 of the syringe 500 filled with a first fluid is seated. Further, referring to FIG. 8, in an apparatus for operating a syringe according to another embodiment of the present invention, the body 100 may include a piston holding assistant portion 160 that helps a user's hand easily hold a piston 560 of the syringe 500 when separating the syringe 500 from the body 100. The piston holding assistant portion 160, as shown in FIG. 6, is formed between the second seat 120 and a third seat 210 and is recessed a predetermined depth on both sides of the body 100. Accordingly, when separating the syringe 500 with a finger under the piston 560, it is possible to easily hold the piston 560 with the finger through the piston holding assistant portion 160, whereby it is possible to easily separate the syringe 500 from the body 100.

Although will be described below, the syringe 500 that is used for the apparatus 10 for operating a syringe according to an embodiment of the present invention is composed of an inner barrel 511 and an outer barrel 512, and the cylinder 520 filled with a first fluid is inserted into the inner barrel 511 from the rear, so a step exists between the cylinder 520 and the lower end of the syringe 500. In the present invention, a step is formed between the first seat 110 in which a syringe body 510 is seated and the second seat 120 in which the cylinder 520 of the syringe 500 is seated in consideration of the structure of the syringe 500, whereby the syringe 500 having a dual pipe structure can be more stably seated in the body 100.

Meanwhile, a mounting groove 130 may be formed in the body 100 at a position corresponding to the position at which a mounting protrusion 590 formed on the bottom of the syringe body 510 is formed, when the syringe body 510 is mounted. The shape of the mounting groove 130 may be a slit shape when the mounting protrusion 590 is a slit-shaped protrusion in accordance with an embodiment, and when the mounting protrusion 590 is a protrusion having a predetermined area in accordance with another embodiment, the mounting groove 130 may be formed a groove shape having the predetermined area. However, these are only examples, and the shape and structure of the mounting groove 130 formed in the body 100 are not limited to specific shape and structure.

As described above, since the mounting groove 130 is formed in the body 100 at the position corresponding to the position of the mounting protrusion 590 formed on the bottom of the syringe body 510, the syringe 500 can be more stably coupled to the body 100.

The actuator 200 is disposed behind the body 100 and can move the piston 560 of the syringe 500 forward and backward such that one or more fluids in the syringe 500 can be selectively discharged. In detail, the actuator 200 includes the third seat 210 in which an end of the piston 560 is seated, and a motor 221, and may include an actuating body 220 that moves the piston 560 forward and backward in surface contact with an end surface of the piston 560 as the motor 221 is operated. In this configuration, the third seat 210 fixes the piston 560 of the syringe 500, thereby being able to keep the piston 560 at the original position even though the actuating body 220 moves.

That is, according to the apparatus 10 for operating a syringe according to the present invention, since the piston 560 of the syringe 500 is seated in the third seat 210 and an end surface of the piston 560 comes into surface contact with the actuating body 220, when the piston 560 is moved forward or backward by operation of the motor 211 included in the actuating body 220, a fluid in the syringe 500 can be discharged through a needle of the syringe 500. By this configuration, the syringe 500 can be automated such that the piston 560 is moved forward or backward, as set, when the actuating body 220 is moved in accordance with an operation instruction programmed in the controller 22 or given by a user.

Referring to FIGS. 3 and 5, the holder 300 is provided on the bottom of the body 100 and holds a finger or the back of a hand of a user, and may be formed in a curved shape having a predetermined area to be able to be supported on the finger or the back of the hand of the user.

In detail, according to an embodiment, the holder 300 may include one or more of a first holder 310 disposed at the front portion of the bottom of the body 100, having a predetermined area to be held on a portion of the finger, and having a curvature in the predetermined area to surround the portion of the finger, and a second holder 320 disposed at the rear portion of the bottom of the body 100, having a predetermined area to be held at a portion between the thumb and the index finger of the back of the hand, and having a curvature in the predetermined area to surround the portion between the thumb and the index finger.

The apparatus 10 for operating a syringe according to the present invention is proposed to solve the problems that are generated when a surgical procedure is performed by manually operating the syringe 500 in the related art, and performs dermal regeneration while discharging a fluid in the syringe 500 using the actuator 200 with the syringe 500 mounted in the body 100. Such dermal regeneration is performed by inserting the needle of the syringe 500 into the skin of a human body and requires high precision and safety, so it is required to stably fix the body 100 without shaking in a surgical procedure.

In order to solve this problem, the apparatus 10 for operating a syringe according to the present invention has the first holder 310 disposed at the front portion of the bottom of the body 100, having a predetermined area to be held on a portion of a finger, and having a curvature in the predetermined area to surround the portion of the finger, and the second holder 320 disposed at the rear portion of the bottom of the body 100, having a predetermined area to be held at a portion between the thumb and the index finger of the back of a hand, and having a curvature in the predetermined area to surround the portion between the thumb and the index finger.

Although will be described again below together with the cover 400, a first hinge portion 140 and a second hinge portion 420, and a first fixing portion 150 and a second fixing portion 420 in the apparatus 10 for operating a syringe according to the present invention are held by a thumb and an index finger of an operator, and in this case, the first holder 310 is held on a portion of a middle finger and the second holder 320 is held at the portion between the thumb and the index finger of the back of the hand, whereby the body 100 can be stably held without shaking in a surgical procedure, and accordingly, precision and safety of a surgical procedure can be improved.

The cover 400 has a shape surrounding the top of the syringe 500, is hinged at a side to the body 100, and covers the syringe 500 mounted in the body 100 by rotating through a hinge, thereby being able to fix the syringe 500 with the body 100.

In detail, the body 100 may further include the first hinge portion 140 hinged on a side to the cover 400 and the first fixing portion 150 fixing the cover 400 on another side, and the cover 400 may include the second hinge portion 410 hinged to the first hinge portion 140 on a side and the second fixing portion 420 fixed to the first fixing portion 150 on another side. According to an embodiment, the first fixing portion 150 and the second fixing portion 420 may be configured such that, as shown in FIG. 2, a protrusion formed at the first fixing portion 150 is fitted in a grooved formed at the second fixing portion 420 to enter a locked state, and when a slider formed at the first fixing portion 150 is slid, the protrusion and the groove are separated. Since the structure of such a locking mechanism is well known in the art, it is not described in detail.

As described above, the first hinge portion 140 and the second hinge portion 410 share a hinge shaft and can rotate on the hinge shaft, and the first fixing portion 150 and the second fixing portion 420 are coupled to each other, thereby being able to fix the syringe 500.

Meanwhile, referring to FIG. 4, the first hinge portion 140 and the second hinge portion 410 may protrude to a side, and the first fixing portion 150 and the second fixing portion 420 may protrude to another side. In this configuration, the first hinge portion 140 and the second hinge portion 410 protrude to a side while having a predetermined area, and the first fixing portion 150 and the second fixing portion 420 and protrude while having over a predetermined area, so when the first hinge portion 140 and the second hinge portion 410, and the first fixing portion 150 and the second fixing portion 420 are held by a thumb and an index finger, the thumb and the index finger can be supported on the first hinge portion 140 and the second hinge portion 410, and the first fixing portion 150 and the second fixing portion 420.

In the present invention, the first hinge portion 140 and the second hinge portion 410, and the first fixing portion 150 and the second fixing portion 420 may be protruded while having a predetermined angle to function as not only hinge portion and fixing portions, but holding portions.

Further, an operator stably holds the apparatus 10 for operating a syringe in a surgical procedure using the first hinge portion 140 and the second hinge portion 410, and the first fixing portion 150 and the second fixing portion 420, whereby it is possible to prevent the body 100 from shaking in a surgical procedure, and accordingly, it is possible to improve precision and safety of a surgical procedure.

Meanwhile, a tube groove 430 that prevents folding of a tube 700 connecting a second fluid injection port 570 and a second fluid supplier 600, and fixes the tube 700 may be formed on the inner surface of the cover 400. Referring to FIGS. 4 to 6, the second fluid injection port 570 that communicates with a filling space 580 through a side of a syringe body 510 such that a second fluid fills the filling space 580 is formed at the top of the syringe body 510. The second fluid injection port 570 and the second fluid supplier 600 can be connected through the tube 700.

In this configuration, when the tube 700 connecting the second fluid injection port 570 and the second fluid supplier 600 is moved or folded, there may be a problem that a second fluid leaks or the second fluid is not normally supplied to the second fluid injection port 570 due to folding of the tube 700.

In order to prevent this problem, the tube groove 430 that can fix the tube 700 is formed on the inner surface of the cover 400 in the present invention, so when the cover 400 is closed, the tube 700 is fixed in the tube groove 430, whereby the tube 700 can be fixed without shaking when the apparatus 10 for operating a syringe is operated. Accordingly, it is possible to prevent the problem that a second fluid leaks or the tube 700 is folded.

Further, an opening 440 having a predetermined area and making it possible to check the remaining volume of fluids in the syringe 500 may be formed at the cover 400. According to the apparatus 10 for operating a syringe of the present invention, when a first fluid is fully discharged from the syringe 500, the cylinder 520 filled with the first fluid should be replaced, and it is possible to easily check the remaining volume of the first fluid by forming the opening 440 at the cover 400. Accordingly, it is possible to easily check the point in time to replace the cylinder 520 filled with the first fluid.

Further, referring to FIG. 8, an assistant groove 450 that assists the cover 400 to be easily opened by fitting a finger or a fingernail therein when opening the cover 400 may be formed at the cover 400. According to an embodiment, the assistant groove 450 may be formed on the side on which the fixing portion is formed at the cover 400 and may be formed to have a predetermined area and a predetermined depth to a side. In other words, when opening the cover 400, a user can hold the cover 400 by fitting a finger or a fingernail into the assistant groove 450 and then can open the cover 400.

Meanwhile, the second fluid supplier 600 is formed on the bottom of the actuator 200 and can supply a second fluid into the outer barrel 512 of the syringe 500 through the second fluid injection port 570. In this configuration, the second fluid injection port 570 and the second fluid supplier 600 may be connected through the tube 700. However, this is only an embodiment, and the second fluid injection port 570 and the second fluid supplier 600 may be connected through other devices than the tube 700.

Referring to FIG. 9, the syringe 500 may include one or more of a syringe body 510, an injector 530, a through-hole 540, a check valve 550, a piston 560, and a second fluid injection port 570.

The syringe 500 may have a cylindrical shape and the body thereof may be composed of an inner barrel 511 and an outer barrel 512. The cylinder 520 filled with a first fluid can be inserted and coupled in the inner barrel 511. The first fluid filled in the cylinder 520 can be discharged to a needle through the internal space of the injector 530 to be described below.

The outer barrel 512 may be spaced a predetermined distance apart from the inner barrel 511 and may surround the inner barrel 511. That is, the diameter of the outer barrel 512 may be larger than the diameter of the inner barrel 511. A filling space 580 that is filled with a second fluid may be formed between the inner barrel 511 and the outer barrel 512. Further, the length of the inner barrel 511 is larger than the length of the outer barrel 512, and a second part 532 is inserted in a space formed by the length difference. A portion of the second part 532 may be sealed in contact with an inner surface of the outer barrel 412 and the other portion may be sealed in contact with the inner surface of the inner barrel 511.

Meanwhile, in the present invention, a first fluid A may include hyaluronic acid as a main component and a second fluid B may include carbon dioxide as a main component.

The injector 530 is coupled to the front of the body of the syringe 500, may form a passage through which a first fluid and a second fluid are discharged, and may be composed of a first part 531 and a second part 532.

The first part 531 is positioned outside the body, and the front end thereof is coupled to a needle and the rear end thereof is sealed in contact with the outer barrel 512. An inclined surface inclined toward the center as it goes from the rear end to the front end may be formed on the side of the first part 531. The inclined surface makes insertion into the skin of a person easy.

The second part 532 is connected to the rear end of the first part 531, and may be inserted in the syringe body 510 and sealed in contact with the inner barrel 511. The second part 532 is inserted in contact with the inner barrel 511 in a space formed by the length difference between the outer barrel 512 and the inner barrel 511.

The through-hole 540 can perform a function of enabling the filling space 580 and the inside of the injector 530 to communicate with each other. The through-hole 540 may be formed on a side of the second part 532 of the injector 530 and may communicate with the filling space 580. Accordingly, a second fluid can flow into the injector 530 through the through-hole 540 from the filling space 580.

The check valve 550, which is a valve that allows a fluid to flow only in one direction and prevents the fluid from flowing in the opposite direction, is disposed in the through-hole 540 and can prevent a fluid from flowing from the injector 530 to the filling space 580 and can allow a fluid to flow from the filling space 580 to the injector 530.

The piston 560 is connected to the actuator 200 and can be moved forward and backward with operation of the actuator 200 such that one or more fluid of a first fluid and a second fluid filled in the syringe 500 are discharged through the needle of the syringe 500.

The second fluid injection port 570 is formed on the top of the syringe body 510 and can communicate with the filling space 580 through the side of the syringe body 510 such that the filling space 580 is filled with a second fluid.

A second fluid storage 21 storing a second fluid to be supplied to the syringe 500 may be provided in the main body 20. Further, according to an embodiment, the controller 22 controlling movement of the piston 560 through the motor 221 included in the actuator 220 of the apparatus 10 for operating a syringe may be provided in the main body 20. According to another embodiment, the controller may be provided in the apparatus for operating a syringe.

In this configuration, a controller 22 can move a piston to follow predetermined motion on the basis of a set mode when recognizing a request to operate or stop the apparatus for operating a syringe.

In other words, the controller 22 can move the piston 560 to follow a predetermined motion on the basis of a set mode when recognizing a request to operate the apparatus 10 for operating a syringe, and can move the piston 560 to follow a predetermined motion on the basis of a set mode when recognizing a request to stop the apparatus 10 for operating a syringe such that one or more fluids of a first fluid and a second fluid are discharged to the needle of the syringe 500.

According to an embodiment, in the system 1 for operating a syringe, requests to operate and stop the apparatus 10 for operating a syringe may be transmitted to the controller through the pedal switch 22.

Meanwhile, in dermal regeneration in which the apparatus 10 for operating a syringe according to the present invention is used, various surgical procedures exists, depending on skins or diseased parts, and for those various surgical procedures, it is required for the controller 22 to control the actuator 200 in various ways.

To this end, the system 1 for operating a syringe according to the present invention may further include a setter 50 that sets motions of the piston 560, and it is possible to set a first mode or a second mode through the setter 50. The motion of the piston 560 according to the first mode or the second mode is described in detail below.

According to an embodiment, when the pedal switch is pressed down and released with the first mode set through the setter 50, the controller 22 can move the piston 560 backward by a preset first distance and then forward by the sum of the preset first distance and a preset second distance, and can move the piston 560 backward by a preset third distance and then forward by a distance shorter than or the same as the third distance.

In the present invention, a syringe may be filled with a first fluid and a second fluid, and in this case, the first distance may be set on the basis of the amount of the second fluid that is discharged from the syringe 500 and the second distance may be set on the basis of the amount of the first fluid that is discharged from the syringe 500.

The first fluid that is used in the present invention may include hyaluronic acid as a main component and the second fluid may include carbon dioxide as a main component. The meaning of the main component is that hyaluronic acid and carbon dioxide are components that account for the most ratio, and depending on cases, means that other kinds of components may also be included.

In other words, when the pedal switch is pressed down and then released with the first mode set, the controller 22 moves the piston 560 forward by a first distance corresponding to the volume of carbon dioxide to be discharged from the syringe 500 and the moves the piston 560 forward by the first distance such that set carbon dioxide is discharged from the syringe 500, thereby tearing a dermal layer. Further, the controller 22 moves the piston 560 forward by a second distance corresponding to the volume of hyaluronic acid to be discharged such that set hyaluronic acid is discharged from the syringe 500, thereby supplying hyaluronic acid into the torn space. In this case, the second distance may be the same as, or smaller or larger than the first distance, depending on surgical procedure situations. In this case, the second distance means a forward movement distance of the piston 560 and the first distance means a backward movement distance of the piston 560.

Further, when the pedal switch is pressed down and then released with the first mode set, the controller 22, as described above, can move the piston 560 backward by a preset first distance, forward by the sum of the preset first distance and a preset second distance, backward by a preset third distance, and then forward by a distance shorter than or the same as the third distance.

As described above, the reason of moving the piston 560 backward by a preset first distance, forward by the sum of the preset first distance and a preset second distance, backward by a preset third distance, and then forward by a distance shorter than or the same as the third distance is:

for removing the remaining volume of a first fluid because when a small amount of first fluid remains in the end or the needle of the syringe 500, it is required to completely remove the remaining first fluid, and then insert the needle and discharge a second fluid.

That is, generalizing the above description, when the pedal switch is pressed down and then released with the first mode set by an operator, the controller 22 moves the piston 560 backward by a first distance, forward by the sum of the preset first distance and a preset second distance, backward by a preset third distance, and then forward by a distance shorter than or the same as the third distance, whereby it is possible to completely remove a small amount of first fluid remaining in the end or the needle of the syringe 500, and then perform next insertion.

As described above, through only a simple operation of pressing down or releasing the pedal switch, the apparatus 10 for operating a syringe is automatically operated such that desired amounts of first fluid and second fluid are discharged from the syringe 500 and the needle is inserted after the first fluid remaining in the end or the needle of the syringe 500 is completely removed before the needle is inserted, whereby it is possible to maintain the amounts of the first fluid and the second fluid that are discharged from the syringe 500 at a constant level, and accordingly, it is possible to minimize differences in surgical procedures.

Meanwhile, when the pedal switch has been pressed down with the second mode set through the setter 50, the controller 22 can move the piston 560 backward by a preset first distance and then forward by the sum of the preset first distance and a preset second distance. In this case, when the pedal switch has been pressed down with the second mode set, the controller 22 repeats the operation of moving the piston 560 backward by the preset first distance and then forward by the sum of the preset first distance and the preset second distance until the pedal switch is released.

Since, as described above, when the pedal switch has been pressed down with the second mode set, the controller 22 repeats the operation of moving the piston 560 backward by the preset first distance and then forward by the sum of the preset first distance and the preset second distance until the pedal switch is released, it is possible to help an operator conveniently concentrate on a surgical procedure without pressing down and releasing the pedal switch 40.

However, when the pedal switch is released with the second mode set, the controller 22 can move the piston backward by the preset third distance and then forward by a distance shorter than or the same as the third distance.

The linkage 30 serves to connect the apparatus 10 for operating a syringe and the main body 20 to each other, maintain the apparatus 10 for operating a syringe hung in the air, and adjust a position and an angle with the apparatus 10 for operating a syringe hung in the air.

In the detail, the linkage 30 may include a first link 31 extending upward from the upper end of the main body 20, a second link 32 extending downward from the upper end of the first link 31, and a third link 33 extending downward from the lower end of the second link 32 and fixing the apparatus for operating the syringe 500 at an end thereof.

As described above, in the system 1 for operating a syringe according to an embodiment of the present invention, the apparatus for operating the syringe 500 is connected to the main body 20 through the linkage 30 and the position and angle thereof can be freely adjusted with the apparatus hung in the air in a surgical procedure process, whereby it is possible to minimize fatigue due to the weight of the apparatus 10 for operating a syringe while an operator performs a surgical procedure.

INDUSTRIAL APPLICABILITY

The present invention relates to a system for operating a syringe and, more particularly, to an apparatus for operating a syringe, the system being able to reduce errors in surgical procedure and enable a more convenient surgical procedure when performing dermal regeneration.

The invention claimed is:

1. A system for operating a syringe, the system comprising:

an apparatus for operating the syringe filled with one or more fluids, the apparatus being configured to receive the syringe and comprising a motor configured to selectively discharge the one or more fluids filled in the syringe by moving forward and backward a piston of the syringe;

a controller configured to control movement of the piston of the syringe through the motor;

a pedal switch configured to transmit requests to operate and stop the apparatus to the controller; and a setter configured to set motions of the piston, wherein the controller is configured to move the piston to follow a predetermined motion based on a set mode when recognizing a request to operate or stop the apparatus, wherein the setter is configured to set a first mode or a second mode, wherein in response to the pedal switch being pressed down and released with the first mode, the controller is configured to move the piston backward by a preset first distance, forward by the sum of the preset first distance and a preset second distance, backward by a preset third distance, and then forward by a distance shorter than or the same as the preset third distance.

2. The system of claim 1, wherein the syringe is filled with a first fluid and a second fluid, and the preset first distance is set based on an amount of the second fluid that is discharged from the syringe and the preset second distance is set based on an amount of the first fluid that is discharged from the syringe.

3. The system of claim 2, further comprising a main body including a fluid storage configured to store the second fluid to be supplied to the syringe.

4. The system of claim 3, further comprising a linkage extending upward from the main body and then extending downward, and configured to maintain the apparatus hung in the air with a needle facing down.

5. The system of claim 4, wherein the linkage connects the apparatus and the main body to each other, is configured to maintain the apparatus hung in the air, and is configured to adjust a position and an angle with the apparatus hung in the air.

6. The system of claim 5, wherein the linkage includes:

a first link extending upward from an upper end of the main body;

a second link extending downward from an upper end of the first link; and a third link extending downward from a lower end of the second link and configured to fix the apparatus at an end of the third link.

7. A system for operating a syringe, the system comprising:

an apparatus for operating the syringe filled with one or more fluids, the apparatus being configured to receive the syringe and comprising a motor configured to selectively discharge the one or more fluids filled in the syringe by moving forward and backward a piston of the syringe;

a controller configured to control movement of the piston of the syringe through the motor;

a pedal switch configured to transmit requests to operate and stop the apparatus to the controller; and a setter configured to set motions of the piston, wherein the controller is configured to move the piston to follow a predetermined motion based on a set mode when recognizing a request to operate or stop the apparatus, wherein the setter is configured to set a first mode or a second mode, wherein, in the second mode, the controller is configured to move the piston backward by a preset first distance and then forward by the sum of the preset first distance and a preset second distance in response to the pedal switch being pressed, and the controller is configured to move the piston backward by a preset third distance and then forward by a distance shorter than or the same as the preset third distance in response to the pedal switch being released.

8. The system of claim 7, wherein, in response to the pedal switch being pressed down with the second mode, the controller is configured to repeat an operation of moving the piston backward by the preset first distance and then forward by the sum of the preset first distance and the preset second distance until the pedal switch is released.

9. A system for operating a syringe, the system comprising:

an apparatus for operating the syringe filled with one or more fluids, the apparatus being configured to receive the syringe and comprising a motor configured to selectively discharge the one or more fluids filled in the syringe by moving forward and backward a piston of the syringe;

a controller configured to control movement of the piston of the syringe through the motor;

wherein the controller is configured to move the piston to follow a predetermined motion based on a set mode when recognizing a request to operate or stop the apparatus, wherein the apparatus includes one or more of:

a body in which the syringe filled with the one or more fluids is mounted, the one or more fluids comprising a first fluid and a second fluid;

an actuator disposed behind the body and configured to selectively discharge the one or more fluids filled in the syringe by moving forward and backward the piston;

a holder provided on a bottom of the body, configured to hold a finger or a back of a hand of a user, and formed in a curved shape having a predetermined area to be able to be supported on the finger or the back of the hand of the user;

a fluid supplier disposed at a bottom of the actuator, connected to a fluid storage, connected to a fluid injection port, and configured to supply the second fluid to an outer barrel through the fluid injection port; and a cover having a shape surrounding a top of the syringe, hinged at a side to the body, and configured to cover the syringe mounted in the body by rotating through a hinge to fix the syringe with the body.

10. The system of claim 9, wherein the syringe includes:

a syringe body comprising an inner barrel that is filled with the first fluid, the outer barrel that surrounds the inner barrel at a predetermined distance from the inner barrel, and a filling space disposed between the inner barrel and the outer barrel; and the fluid injection port formed at the syringe body and communicating with the filling space such that the filling space is filled with the second fluid.

11. The system of claim 10, wherein a mounting protrusion for mounting in the body is formed on a bottom of the syringe and one or more mounting grooves are formed in the body at a position corresponding to a position of the mounting protrusion when the syringe is mounted.

12. The system of claim 9, wherein the holder includes one or more of a first holder disposed at a front portion of the bottom of the body, having a predetermined area to be held on a portion of the finger, and having a curvature in the predetermined area to surround the portion of the finger, and a second holder disposed at a rear portion of the bottom of the body, having a predetermined area to be held at a portion between a thumb and an index finger of the back of the hand, and having a curvature in the predetermined area to surround the portion between the thumb and the index finger.

13. The system of claim 9, wherein the body further includes a first hinge portion hinged to the cover at a side and a first fixing portion configured to fix the cover at another side, the cover includes a second hinge portion coupled to the first hinge portion at a side and a second fixing portion fixed to the first fixing portion at another side, and the first hinge portion and the second hinge portion share a hinge shaft and are configured to rotate on the hinge shaft, and the first fixing portion and the second fixing portion are coupled to each other to fix the syringe.

14. The system of claim 13, wherein the first hinge portion and the second hinge portion protrude to a side, the first fixing portion and the second fixing portion protrude to another side, and a thumb and an index finger are supported on the first hinge portion and the second hinge portion, and the first fixing portion and the second fixing portion.

15. The system of claim 9, further comprising a tube groove formed on an inner surface of the cover and configured to prevent folding of a tube connecting the fluid injection port and the fluid supplier to each other, and to fix the tube.

* * * * *